United States Patent [19]
Vorobieva

[11] Patent Number: 5,889,048
[45] Date of Patent: Mar. 30, 1999

[54] METHODS AND COMPOSITIONS FOR TREATING DEFECTIVE CELL FUNCTIONS

[76] Inventor: Tamara Vasilievna Vorobieva, Novopetrovskaya, 7-21, Moscow, 125239, Russian Federation

[21] Appl. No.: 693,041

[22] PCT Filed: Jun. 15, 1994

[86] PCT No.: PCT/RU94/00128

§ 371 Date: Aug. 19, 1996

§ 102(e) Date: Aug. 19, 1996

[87] PCT Pub. No.: WO95/22336

PCT Pub. Date: Aug. 24, 1995

[30] Foreign Application Priority Data

Feb. 18, 1994 [RU] Russian Federation ............. 94004903
Feb. 18, 1994 [RU] Russian Federation ............. 94004904

[51] Int. Cl.$^6$ ...................... A61K 31/305; A61K 31/285; A61K 31/185

[52] U.S. Cl. ........................ 514/496; 514/504; 514/578; 514/825; 514/855

[58] Field of Search ..................................... 514/496, 504, 514/578, 825, 855

[56] References Cited

U.S. PATENT DOCUMENTS 4,104,373  8/1978  Sichert ..................................... 424/195

OTHER PUBLICATIONS

CA 94:317, Herr et al, 1980.

*Primary Examiner*—Kimberly Jordan
*Attorney, Agent, or Firm*—Dykema Gossett PLLC

[57] ABSTRACT

A pharmaceutical formulation having immunomodulating and regenerating effect on abnormal function of cell tissue division-regulating system comprises, as an active ingredient, mercury dichloride or potassium arsenite or sodium arsenate in the amount of 0.01–1.5% by weight and of a diluent up to 100% by weight. The proposed pharmaceutical formulation preferably contains natural white grape wine with sugar content of 3–4% by weight or whey with sugar content of 3–4% by weight as the diluent.

5 Claims, No Drawings

METHODS AND COMPOSITIONS FOR TREATING DEFECTIVE CELL FUNCTIONS

This application is a 371 of PCT/RU94/00128, filed Jun. 15, 1994 published as WO95/22336, Aug. 24, 1995.

FIELD OF THE INVENTION

The preset invention relates to medicine and, more particularly, it relates to novel immunomodulator having regeneration effect on abnormal function of cell tissue division-regulating system.

DESCRIPTION OF THE PRIOR ART

Known in the art is a variety of immune response-modulating agents. Thus for example, the capacity of stimulating immune responses in the body (including lenkopoiesis) exibits nucleic acid derivatives; the capacity of activating specifically immunocompetent cells (T and B-lymphocytes) have pyrogenal, prodigiosan and the like. It is well known that levamisole, (−) 2,3,5,6-tetrahydro-6-phenylimidazo|2,1-b|-thiazole hydrochloride can stimulate selectively the regulatory T-lymphocyle function, enhance poor reaction of cell-mediated immunity, supress brisk antibody response, with it having no effects on normal reaction (M. D. Mashkovsky, "Pharmacinticals", Moscow, "Medicine", 1992, V. 2, p. 169–170)

There is also known in the art a medicinal agent, thymaline (complex of polypeptide fractions isolated from cattle thymas gland), which can regulate T and B lymphocyte production, stimulate the cell-mediated immune responses and promote regeneration processes (M. D. Mashkosvsky, "Pharmaceuticals", Moscow, "Medicine", 1992, V. 2, p. 171)

This medicinal agent is used as an immunostimulant and biostimulant in treatment of disorders associated with weakning the cell-mediated immunity including acute chronic purulent processes and inflammations, burn disease. It is also suited to use to use at conditions associated with suppression of immune and blood formation function in oncologic patients after a radiation therapy or chemotherapy.

However, all of the above-mentioned medicinal agents are faulty for their selective action, toxicity, a number of adverse effects and contradictions for administration.

It is well known by those skilled in the art that a key stage of tumor formation is associated with failure of cell division-regulating system.

There are a great variety of antineoplastic agents that are compounds having different chemical structures. Such compounds can be synthesized via chemical reactions or they can be prepared by isolation of biologically active substances from raw materials of vegetable and animal origin (M. D. Mashkovsky, "Pharmaceuticals", Moscow, "Medicine", 1992, v.2, pp. 423–468). Such antineoplastic agents include cyclophosphamide, sarcolysine, mustargen, caryolysine and the like. The alkylating properties of such agents are of considerable importance in mechanism of their action. They are capable of reacting with nucleophilic centers of protein molecules such that DNA synthesis is disturbed, resulting in abnormal vital activity of cells and inhibition of their mytotic division.

Known in the art are antitneoplastic ethylenimine-containing agents such as thiophosphamide, dipine, benzoteph and the like which are compounds that have cytostatic and suppressive effect on proliferating tissue including malignant tissue.

The disturbance of nucleic acids metabolism and the blocking of mitotic cell division are of great concern in the mechanism of action of such medicinal agents.

Among antineoplastic agents, a few of antibiotics are in wide use, more particularly semi-synthetic derivatives wherein nuclei of molecules from the known antitumor antibiotics are used. The effector mechanism of such medicinal agents is associated with selective inhibition of DNA-dependent RNA synthesis, resulting in disturbance of nucleic acid production.

However, most of antitumor agents mentioned above are faulty for their high toxicity, adverse effects (suppression of blood formation). No antineoplastic agents which could regenerate the defective function of cell tissue division-regulating system has previously been reported.

Mercury-containing compounds are widely used in medicine as antiseptics, such as mercury dichloride. Known in the art is the use of arsenic-containing preparations (sodium arsenate and potassium arsenite) for treatment of patients suffered from hematological diseases due to their capacity of inducing bone marrow erythropoiesis and suppressing leukopoiesis.

However, the above-mentioned pharmaceuticals have not been proposed to use as an immunomodulating or regenerating agent in conditions associated with defective function of cell tissue division-regulating system.

DISCLOSURE OF THE INVENTION

The invention is based on the problem of providing novel immunomodulating agent having a regenerating effect on abnormal defective function of cell tissue division-regulating system, high efficiency, low toxicity and wide spectrum of its action.

The problem is solved by providing a pharmaceutical formulation of the present invention, which has an immunomodulating and regenerating effects on abnormal function of cell tissue division-regulating system, comprising an active ingredient and a diluent, with the active ingredient being mercury dichloride or potassium arsenite, or sodium arsenate, at the following mixture ratio, % by weight

| | |
|---|---|
| mercury dichloride or potassium arsenite or sodium arsenate | 0.01 – 1.5 |
| diluent | up to 100.0 |

A pharmaceutical formulation of the present invention includes preferably, as a diluent, dry white grape wine with sugar content of 3–4% by weight or whey with sugar content of 3–4% by weight.

The reversible coagulated vegetable proteins with released SH-groups of dry white grape wine and reversible coagulated proteins of whey, contained in small amounts, are blocked by mercury or arsenic ions, thereby eliminating toxicity of the proposed pharmaceutical formulation.

3–4% content of sugars in the wine and whey assists to maintain acid fermentation medium and improves the gustatory quality of the proposed pharmaceutical formulation.

The preferred embodiments of a pharmaceutical formulation of the invention are as follows.

A pharmaceutical formulation of the invention for internal or external use contains the following ingredients, % by weight

| | |
|---|---|
| mercury dichloride | 0.01–0.1 |
| dry white grape wine sugar content of 3–4% by weight or whey with of sugar content of 3–4% by weight up to | 100.0 |

A pharmaceutical formulation of the present invention for internal or external use containing as the diluent a mixture of pork fat, natural honey and ethyl alcohol, includes the following ingredients, % by weight:

| | |
|---|---|
| mercury dichloride | 0.03–0.13 |
| pork fat | 30.7–37,3 |
| natural honey | 30.7–37,3 |
| ethyl alcohol | up to 100.0 |

A pharmaceutical formulation of the invention for internal use, which may be preferably used for treatment of acute and chronic leukosis, includes the following ingredients, % by weight:

| | |
|---|---|
| sodium arsenate or potassium arsenite | 0.05–0.15 |
| dry white grape wine with 3–4% sugar content or whey with 3–4% sugar content | up to 100.0 |

The use of such pharmaceutical formulation of the present invention is preferable for treatment of acute and chronic leukosis, since the main depot of arsenic accumulation is blood.

A pharmaceutical formulation of the invention for external use includes the following ingredients, % by weight:

| | |
|---|---|
| mercury dichloride | 0.3–1,5 |
| dry white grape wine with 3–4% sugar content or whey with 3–4% sugar content | up to 100.0 |

Such pharmaceutical formulation of the present invention has no toxicity because of the capacity of mercury/arsenic ions to block reversibly sulfolhydryl groups (SH) for which, of all reactive groups, such ions have the highest affinity.

The general property for all organisms and tumors is cell division which is triggered by a signal of special macromolecules, namely growth factors and transferred through protein molecules or receptors.

The structure of molecules of all growth factors and immunoglobulins, cylokines, receptors of lymphocytes and erythrocytes as well as several hormones (insulin, vasopressin and the like) is characterized by disulfide bridges that are hydrolyzable (with bond breakage ) in the presence of mercury ions, no matter whether other functional groups are present or not.

The structure of molecules of all cytoplasm receptors and more than two tens of enzymes (including proteolytic enzymes) is the presence of free SH-binding sites.

The reversibly Hg/As-protected SH-groups of receptors for growth factors mercury or arsenic ions, steroid hormones and adrenergic receptors provides the inhibition of a new growth.

The double antitumor protection is provided by the breakage of the disulfide bonds of growth factors, immunoglobulins and lymphocyte/erythrocyte receptors in the presence of mercury and arsenic ions.

The immune-response modulating activity of a pharmaceutical formulation of the invention is attained by the breakage of the disulfide bonds of immunoglobulins, some hormones (insulin, vasopressin), cytokines and lymphocyte/erythrocyte receptors.

Reversible blocking of SH-groups in enzymes and receptors by action of a pharmaceutical formulation of the invention provides the protection of the body from radiation exposure.

Assuming that on tumor cell surfaces there are growth factor receptors 20–100 times as high as on those of any other cell, and a functional group of growth factor receptors is SH-group to which mercury ions have the highest affinity, it is evident that the effect of the proposed formulation on tumor cells is 20–100 times stronger.

The active ingredient of the proposed pharmaceutical formulation, mercury dichloride, when dissolved, has no conductance (in nonionized state), and its nonionized molecules are permeabilizable easily through the membranes, including brain, and enter the cytoplasm having lower pH, while all abnormal cells including tumor cells have anomalously low pH values, and because of rising acid number it is only those cells which take up mercury, thereby providing a selective effect on pathogenic cells. A pharmaceutical formulation of the invention, by virtue of the above mechanism, can regenerate the defective function of cell tissue division-regulating system. The proposed pharmaceutical formulation exhibits an immune response-modulating activity. By action of the proposed pharmaceutical formulation, there occur the rearrangement of internal regulatory mechanisms combining immunocompetent cells into a single system, and the normalization of immunologic parameters.

THE BEST MODE OF CARRYING OUT THE INVENTION

A pharmaceutical formulation of the invention includes, as an active ingredient, mercury dichloride or potassium arsenite, or sodium arsenate in an amount of 0.01–1.5% by weight and a pharmaceutically acceptable diluent. A pharmaceutical formulation of the invention for internal and external use contains preferably mercury dichloride in an amount of 0.01–0.1% by weight, using as the diluent dry white grape wine with sugar content of 3–4% by weight or whey with sugar content of 3–4% by weight. Alternatively, a pharmaceutical formulation of the invention includes mercury dichloride in an amount of 0.03–0.13% by weight and a mixture of pork fat, natural honey and ethyl alcohol as the diluent. The above-specified amounts of mercury dichloride have been chosen in experiments to provide the efficiency of the proposed pharmaceutical formulation. It is undesirable that the content of mercury dichloride be lower or higher than the limit values specified above, since the required effect will not be achieved.

According to the invention, when administered per os for treatment of acute and chronic leukosis, a pharmaceutical formulation of the invention is preferred to contain sodium arsenate or potassium arsenite as the active ingredient in the amount of 0.05–0.15% by weight and dry white grape wine with sugar content of 3–4% by weight or whey with 3–4% sugar content as the diluent.

The above-specified amounts of active ingredients have also been chosen in a way of experiments to provide the efficiency of a pharmaceutical formulation of the invention. A pharmaceutical formulation of the invention stimulates numerous various functions of the body, inhibits the oxidative processes, provides the increase in nitrogen and phosphorus assimilation, thereby limiting the protein cleavage, improves metabolic process in tissues and cells and patient's general conditions, rises the hemoglobin percent and number of red blood cells.

A pharmaceutical formulation of the invention for external use application includes the active ingredient, mercury dichloride, in the amount of 0.3–1,5% by weight and the diluent, namely dry white grape wine with sugar content of 3–4% by weight or whey with sugar content of 3–4% by weight As the dry white wine, there is suited to use one of the following check wines "Mutsvani", "Sovinjon" and the like The production process of such wines comprises the step of heat treatment at 60° C., which is necessary to stop partial sugar fermentation. At such temperature, there occur reversible coagulation of vegetable proteins which are present in small amounts in wine product, resulting in release of protein SH-groups that are reversibly protected with mercury or arsenic ions. This makes the solution non-toxic.

The whey also contains coagulated proteins with released SH-groups to be protected reversibly by mercury or arsenic ions. This makes the toxicity of the solution reduce to zero.

A pharmaceutical formulation of the invention can be recommended for treatment of the following diseases: all types of innocent tumors; all types of malignant tumors; various immunodeficient conditions; rheumatism; rheumatoid arthritis; polyarthritis; bronchial asthma; systemic lupus erythematosis; gastric ulcera; gravitational ulcera; herpes; psoriasis; intestinal infection; neurodermite and the like.

The choice of appropriate pharmaceutical formulation of the invention and the duration of its administration can vary from the form and duration of disease, the drug tolerance and other individual peculiarities of patient's body, whereas one should follow a few of requirements during the treatment. For example, one should keep some diet restrictions with excluding such food products as meat, fish, eggs, since during the treatment with a pharmaceutical formulation of the invention there occur the protection of SH-groups in the system of proteolytic enzymes, that is to say the capabilities of the organism to digest protein food become low.

Usually, the course of treatment includes the administration of the proposed pharmaceutical formulation per os according to following regimen: the first three days—5 ml (or 5 g) 3 times a day, then 10 ml (or 10 g) for one month 3 times a day. Simultaneously with or without oral administration, the pharmaceutical formulation may be preferably used as lotions, tampons, syringings and enemas. The appropriate locus to be treated is chosen depending on the localization of a pathologic process, with the proposed formulation applied to coccygeal bone, groin lymph nodes, axilla, backbone, joints, localized neoformations, integmentary or bone-joint tissues. Thus for example, in treatment of mammary gland or female genitals, a pharmaceutical formulation of the invention, along with oral administration, may be used as lotions and vaginal tampons, as well as enemas. In treatment of stomach disorders a pharmaceutical formulation of the invention, along with oral administration, may be applied as lotions to axilla and coccygeal bone and enemas, as well. In treatment of adenoma, a pharmaceutical formulation of the invention, along with administration per os, should locally be applied as lotions to coccygeal bone, groin and axillary lymph nodes. In myeloid leukemia, along with oral administration, the proposed pharmaceutical formulation is be given per os and applied as lotions to coccygeal bone, chest, groin and axillary lymph nodes, backbone, articulations.

In treatment of soft tissue damages and osteogenic sarcoma a pharmaceutical formulation of the invention, along with oral administration is preferably be applied locally as lotions to coccygeal bone, groin and axillary areas, backbone.

A pharmaceutical formulation of the invention with increased mercury content is used for treatment of pulmonary malignant diseases with pus and blood in the sputum.

A pharmaceutical formulation of the invention comprising mercury dichloride as the active ingredient showed to advantage in treatment of skin disorders such as psoriasis and neurodermite. This is most likely to be associated with immune response-modulating properties of a pharmaceutical formulation of the invention which, when externally used, exhibits also an antiinflammatory and repairing effects.

The use of a pharmaceutical formulation of the invention, comprising mercury dichloride as the active ingredient in treatment of gravitational ulcers showed the improvement under administration of the preparation per os following the general regimen together with applying it locally as lotions. The duration of treatment course is 1 month. The treatment, if required, may be repeated in 1 month.

A pharmaceutical formulation of the invention is prepared by conventional methods by mixing the starting materials.

A pharmaceutical formulation of the invention was studied in experiments on animals and tested clinically in human beings.

The test for acute toxicity of a pharmaceutical formulation according to the invention was conducted on 192 healthy male unbred rats (body weight of 180–220 g ) under standard conditions of feeding and keeping. 24 hours before and during the study, the test animals were kept under constant temperature and air ventilation in vivarium. 2 hours prior to the start of the study the animals were deprived of water and food.

The acute toxicity ($LD_{50}$) for each pharmaceutical formulation of the invention to be administered orally or intraperitoneally to provide high toxic effect was determined by the Litchfield-Wilcockson method.

By weighing and screening animals, there were selected 10 rat groups, which were given a pharmaceutical formulation of the invention (liquid forms including dry white wine or whey). Each group included 6 animals.

Rat groups were given intraperitoneally 5; 4; 3; 2 and 1 ml of the proposed pharmaceutical formulation, which amounts corresponded to the following doses of an active ingredient-1.65; 1.32; 0.99; 0.66 and 0.33 mg/kg. In addition, the proposed pharmaceutical formulation was administered orally to the test animals in an amounts of 2; 1,5; 1 and 0.5 ml that corresponded to the following doses of the active ingredient-0.66; 0.495; 0.33 and 0.165 mg/kg. Control animals were given appropriate diluents, namely, dry white grape wine or whey.

The test animals were under observation for 14 days after the treatment with the proposed pharmaceutical formulation. To this end, the evaluation of the general condition, behavior and body weight of test animals was conducted.

Upon administering the proposed pharmaceutical formulation in the above-indicated doses, there was observed the decrease in motor activity and feeling of sleepiness in rats. All such manifestations were more pronounced when animals had been given the proposed formulations intraperitoneally. It was observable, however, no fatal outcome within a few of the first days after administration of the preparation. In addition, when the proposed pharmaceutical formulation (liquid form containing, alternatively, the wine or whey) had been given orally, there was noted no fatal outcome during all the period of observations. No difference of body weight, the general condition and behaviour was observed in the test animals as compared with control.

The identical results were also obtained when the pharmaceutical formulation(dry wine as the diluent) had been given to the animals intraperitoneally, with no fatal outcome observed. It was observed also no significant difference in body weight and behavior of the test animals as compared to control.

The lack of fatal cases, when the animals had been given the proposed pharmaceutical formulation (liquid form containing dry wine as the diluent) orally or intraperitoneally, even though at the maximum permissible amounts, did not allow one to estimate the key parameter of acute toxicity, $LD_{50}$, indicating the low toxicity of those forms of the preparation in such way of administration and at the dosage specified above.

Upon administering a pharmaceutical formulation of the invention (liquid form including whey) intraperitoneally, there were noted the fatal cases at day 5, 6, 7, 8 and 9 after the injection of the preparation. In the animals, prior to their deaths, there were observable some flabbiness, paraplegia and abnormality in hairy coat. In the survived rats, those manifestations were less pronounced, and on day 14 there was noted no significant difference in their 1 behavior and body weight as compared with control.

The evaluation of animal death recurrences, performed by the Litchfield-Wilcockson method, allowed one to estimate $LD_{50}$ for the pharmaceutical formulation (containing whey as the diluent) under the administration of the preparation intraperritoneally In rats, the $LD_{50}$, when the animals had been given the proposed pharmaceutical formulation (liquid form containing whey) intraperitoneally, is 5.8 (1.98–8.8) mg/kg of body weight.

The antiinflammatory activity of a pharmaceutical formulation of the invention was tested with using reinoculated tumor cell cultures.

In the studies a reinoculated leukocyte culture of L-41 strain was used.

The cell culture was incubated by the conventional method. The inoculate density was $1-10^5$ cells in 1 ml of nutrient medium. The nutrient medium was prepared by using equal proportions of media 199 and Eagle, supplemented with 10% bovine serum and antibiotics (100 parts of penicillin and 50 parts of streptomycin per 1 ml of medium. A pharmaceutical formulation of the invention, the diluent (alone), "Erety" wine, and the active ingredient, mercury dichloride, were diluted in the protein-free nutrient medium and added at different concentrations to 3–4 cultures to contact with cell monolayer. Since the active ingredient of a pharmaceutical formulation of the invention is mercury dichloride, we, in our preliminary experiment, have found that $ED_{50}$ of mercury dichloride was <10 µg/ml. On day 2 from the start of the study, a biological activity of the proposed formulation was estimated using 4-point scale. The assays for protein in cultures were performed by the Louri method modified by the Oyama and Eagle.

The cytostatic activity of the proposed formulation was evaluated as the % inhibition of cell culture growth by the suppression of protein production.

According to the existing standard techniques for screening the antitumor preparations, a pharmaceutical formulation is recognized to be efficient when its $ED_{50}$ is less or equal to 100 µg/ml.

The studies has been showed that $ED_{50}$ of the proposed pharmaceutical formulation is 10 µ/ml. This value is 10-fold high the standard, indicating the pronounced cytostatic effect of the preparation on tumor cell cultures.

TABLE 1

Comparison of biologic activity of the proposed pharmaceutical formulation, diluent (dry white grape wine with sugar content of 4% by weight) and active ingredient, mercury dichloride, on the reinoculated tumor culture of L-41 cell line

| Preparation 1 | Mercury dichloride concentration, µg/ml 2 | Alcohol content, % 3 | Protein content, µg/ml 4 | % of cell growth inhibition/ promotion 5 | SD, P 6 |
|---|---|---|---|---|---|
| 1. Control | — | — | 294.0 ± 10.4 | — | |
| 2. Proposed formulation | 1.1 | 0.03 | 318.0 ± 0 | 7.5 promotion | |
| 3. Proposed formulation | 3.3 | 0.1 | 238.3 ± 9.1 | 18.9 inhibition | >0.05 |
| 4. Proposed formulation | 4.9 | 0.15 | 224.0 ± 0 | 23.8 inhibition | >0.05 |
| 5. Proposed formulation | 6.6 | 0.2 | 214 ± 0 | 27.2 inhibition | >0.05 |
| 6. Proposed formulation | 9.9 | 0.3 | 144 ± 0 | 51.0 inhibition | >0.05 |
| 7. Dry white wine | — | 0.03 | 316 ± 25.1 | 6.9 stimulation | |
| 8. Dry white wine | — | 0.1 | 318.0 ± 0 | 7.5 stimulation | |
| 9. Dry white wine | — | 0.15 | 318.0 ± 0 | 7.5 stimulation | |
| 10. Dry white wine | — | 0.2 | 322.5 ± 5.6 | 8.8 stimulation | |
| 11. Dry white wine | — | 0.3 | 307.0 ± 13.8 | 4.2 stimulation | |
| 12. Mercury dichloride | 1.0 | — | 390.3 ± 2.6 | 1.2 inhibition | >0.05 |
| 13. Mercury dichloride | 3.3 | — | 279.0 ± 27.3 | 5.1 inhibition | >0.05 |
| 14. Mercury dichloride | 5.0 | — | 256.0 ± 5.2 | 12.9 inhibition | >0.05 |
| 15. Mercury dichloride | 8.0 | — | 154.0 ± 5.0 | 47.6 inhibition | >0.05 |

From the above data one can see that the pharmaceutical formulation of the invention has the pronounced inhibiting effect on tumor cultures at the concentration of 9.9 µg/ml, as is its $ED_{50}$. $ED_{50}$ of mercury dichloride is about 8 µg/ml. Att the studied concentrations the wine has a slight stimulating effect of 4.2–8.8%.

The study of the immunopharmacologic properties of the proposed pharmaceutical formulation were performed.

The effect of the pharmaceutical formulation of the invention on the weights of main immunologic organs was studied.

The experiments were conducted on the rats of CBA/ C57B1 cell lines and hybride lines of the first generation.

The pharmaceutical formulation of the invention (alternatives containing the wine and whey as the diluent) was administered to rats, C57B1 line as well as the hybrid CBA×C57B1 lines of the first generation for 10 days. 24 hours after the administration of the last dose of the proposed pharmaceutical formulation, the animals were weighed and killed, their spleens were extracted and weighed.

The spleen weights and weight coefficients are shown in Table 2.

TABLE 2

Effect of the proposed, pharmaceutical formulation on spleen weights

| | | | Spleen Weights | | |
|---|---|---|---|---|---|
| N/n 1 | Preparation 2 | Number of animals in group 3 | mg 4 | Significant difference (P) to Control 5 | Weight coefficient 6 | Significant difference (P) to Control 7 |

C57B1 line

| | | | | | | |
|---|---|---|---|---|---|---|
| 1. | Control | 23 | 86 | | 0.55 | |
| 2. | Proposed formulation (milk whey as diluent) | 9 | 90 | >0.5 | 0.53 | >0.05 |
| 3. | Proposed formulation (wine as diluent) | 10 | 87 | >0.5 | 0.51 | >0.5 |

Hybrid of CBA xC57B1 line, first generation

| | | | | | | |
|---|---|---|---|---|---|---|
| 1. | Control | 25 | 114 | | 0.46 | |
| 2. | Proposed formulation (whey as diluent) | 11 | 112 | >0.5 | 0.48 | >0.05 |
| 3. | Proposed formulation (wine as diluent) | 12 | 114 | >0.05 | 0.46 | >0.05 |

The data of these experiments show that a pharmaceutical formulation of the invention has no effect on spleen weight and spleen weight coefficient upon administration for 10 days.

In further experiments the proposed pharmaceutical formulation was injected for 30 day, then, the thymuses were extracted and weighted; mice CBA lines were used in such experiments.

Table 3 shows that the proposed pharmaceutical formulation had no effect on thymus weight at such experimental conditions.

TABLE 3

Effects of the proposed pharmaceutical formulation on thymus weights (wine diluent)

| | Number of animals in group | Thymus Weights mg | Significant difference (P) to Control |
|---|---|---|---|
| Preparation | | | |
| Control | 8 | 174 | |
| Proposed formulation | 7 | 170 | >0.05 |

The effect of the proposed pharmaceutical formulation on graft-versus-host reaction was studied. These studies were performed according to the following procedure.

The hybrid mice, the first generation of CBA/ C57B1 lines, there were; the same amount of syngenic lymphatic cells of the hybrids was injected into mice contralateral paw. On day 8 after the reinoculation of donor lymphatic cells, there were determined the mass of popliteal lymph nodes of both recipient paws. The reaction was estimated by immune reaction index (RI) calculated according to the following formula:

$$RI = \frac{\text{lymph node weight upon injecting } C57B1 \text{ cells}}{\text{lymph node weight upon injecting hybrid cells}}$$

The proposed pharmaceutical formulation (as the diluent there were alternatively used the whey and wine) was injected to both donors and recipients for 10 and 20 days, respectively. The experimental data are given in Tables 4–5.

TABLE 4

Effect of the proposed pharmaceutical formulation (whey diluent) on weights of popliteal lymph nodes in graft-versus-host reaction

| Administration regimen of the proposed formulation | | Number of animals in group | Lymph node weights (mg) | | Reaction index |
|---|---|---|---|---|---|
| recipient (days) | donor | | Control paw | Test paw | |
| 1 | 2 | 3 | 4 | 5 | 6 |
| Control | | 8 | 2.8 | 9.2 | 3.35 |
| 14 | 10 | 9 | 7.2 | 7.7 | 1.10 |
| 14 | 20 | 10 | 11.5 | 13.3 | 1.24 |
| Control | | 11 | 3.3 | 7.1 | |
| 14 | — | 9 | 5.2 | 6.6 | 2.4 |
| — | 10 | 10 | 6.0 | 7.0 | 1.3 |
| 14 | 10 | 10 | 5.2 | 6.6 | 1.4 |

TABLE 5

Effect of the proposed pharmaceutical formulation (wine diluent) on weights of popliteal lymph nodes in graft-versus-host reaction

| Administration regimen of the proposed formulation | | Number of animals in group | Lymph node weights (mg) | | Reaction index |
|---|---|---|---|---|---|
| recipient (days) | donor | | Control paw | Test paw | |
| 1 | 2 | 3 | 4 | 5 | 6 |
| Control | | 11 | 3.3 | 7.1 | 2.4 |
| 14 | — | 9 | 6.7 | 8.2 | 1.3 |
| — | 10 | 10 | 4.6 | 6.2 | 1.4 |
| 14 | 10 | 9 | 5.1 | 6.3 | 1.2 |

Tables 4 and 5 show that the proposed pharmaceutical formulation has a potent effect on cell-mediated immunity in graft-versus—host reaction.

The specificity of the action of the pharmaceutical formulation according to the invention influence is that its effect is attained with injecting such preparation to both recipients and donors. In all of the cases there occur the increase in lymph node weights upon grafting the cells of the same mice line These "control" lymph nodes reach the weights of those as tested, i.e. wherein the response is accomplished by parent lymphoid cells of the parental strain against the genotype cells of such hybrids.

The weights of these "experimental" lymph nodes are substantially identical in all animal groups, including mice that were not given the proposed formulation. Therefore, the proposed pharmaceutical formulation, when injected to both donors and recipients for 10 days, has no effect on weights of those lymph nodes wherein the reaction of donor lymphocytes against the cells of heterologous genotype occurs, but has the stimulating effect on the lymphocyte responses against the cells of their own genotype. In such character of action of the preparation, reaction index is slightly higher than that of test groups.

With prolonging the duration of administration of the proposed pharmaceutical formulation up to 20 days, the weights of both lymph nodes ("experimental" and "control") increases and becomes larger than those of animal the group that was not given such preparation (Table 4). However, these lymph nodes are differed each other insignificantly and the reaction index is 1.24.

The effect of the proposed pharmaceutical formulation on production of rosette-forming cells in mice spleen has been studied. The population of the rosette-forming cells is mixed type, and their determination, as the experience shows, is one of the most sensitive tests in studying immunotropic effects of variety of chemical compounds.

The effect of a pharmaceutical formulation of the invention on production of rosette-forming cells in spleens was determined in mice of opposite lines immunized by sheep erythrocytes. The courses of treatment with different duration of administration of the proposed pharmaceutical formulation began prior to animal immunization with test antigen and continued for 5 days after antigen challenge. On day 7 after antigen challenge, mice were killed and production of cells binding sheep erythrocytes were determined.

The test data indicate that the proposed pharmaceutical formulation 10 and 20 days after the oral administration of it to mice in therapeutically effective dose decreases in production of spleen antigen-binding cells in mice, both animal high and low immune-responsing lines. In case of low immune-responsing lines of animals the decrease of immunoreactivity is more pronounced.

The effect of the proposed pharmaceutical formulation on production of antibody-forming cells in mice spleen was evaluated in testing the degree of influence of the pharmaceutical formulation on the contents of spleen hemolysin-producing cells in animals immunized by sheep erythrocytes. The courses of treatment with different duration of administration of the proposed pharmaceutical formulation began prior to animal immunization with test antigen and continued for 3 days after antigen challenge. The preparation was administered to animals per os in therapeutically equivalent dose, daily. On day 5 after mice immunization with sheep erythrocytes, the animals were killed and the production of spleen antibody-producing cells were determined.

The test data showed that a pharmaceutical formulation of the invention provided the decrease in level of spleen antibody-forming cells in mice of both low- and high immune-responsing lines upon challenge of animals with sheep erythrocytes as test-antigen. In such a case, the level of decreasing the hemolysin-producing cells depends on the duration of administration of the proposed preparation. This decrease becomes significant upon administration of the pharmaceutical formulation for 20 days in both animal lines.

The effect of a pharmaceutical formulation of the present invention on production of circulating antibodies in blood was evaluated 10 and 20 days after the administration of such preparation and 7 days after mice immunization with sheep erythrocytes. The courses of treatment with different duration of administration of the proposed pharmaceutical formulation began prior to animal immunization with test antigen and continued for 5 days after antigen challenge.

The results obtained showed that the proposed pharmaceutical formulation had no effect on such antibody response in studying the immunoreacivity upon oral administration of the preparation for 10 and 20 days in therapeutic dose.

Thus, the content of antibodies, the most integral value of immunoreactivity, remains within the normal (control) level upon administration of the proposed pharmaceutical formulation.

In addition, the effect of a pharmaceutical formulation of the present invention on duration of hexenal sleep, as being a measure of functional state of monooxygenase system in the body was studied.

The experiments were carried out on male inbred mice with body weight of 20–22 g. The proposed pharmaceutical formulation was administered to animals orally for 1–3 weeks, daily; control group was given the same amount of physiological solution. The test-metabolite (hexenal) was injected intraperitoneally in a dosage of 70 mg/kg and the duration of narcotic state in test mice was evaluated.

The results obtained showed that oral administration of the pharmaceutical formulation of the invention in therapeutic dose for 1 or 3 weeks has no effect on the duration of hexenal metabolism, indicating the lack of significant reactions from enzymatic microsomal system in the body.

Based on studying certain immunopharmacologic properties of the pharmaceutical formulation, it has been revealed the significant immunotropic effect of the preparation to cell-mediated immune response or graft-versus-host reaction. Under action of the proposed formulation, there occurred the lymphocyte stimulation in both graft-versus-host reactions (3-weeks administration) and reactions against the cells of the same genotype whereas presenting at another species (10 and 20-days administration). These results were obtained upon administration of the pharmaceutical formulation to both recipients and donors.

In experimental conditions, a pharmaceutical formulation of the present invention inhibited the rosette cell immune response and decreased the titer of antibody-producing cells in mice spleens. However, the integral performance of cell-mediated immunity, namely, the circulating antibody titers retained within the level of control in the test groups.

In therapeutic doses, the proposed pharmaceutical formulation has no effect on functional activity of enzymatic monooxygenase system which, together with the immune system, is a integral part of the the system responsible for patient's body reaction to the action of external factors. This is an additional evidence of a soft immunotropic effect of the proposed pharmaceutical formulation.

The evaluation of the capacity of the proposed pharmaceutical formulation to induce mutagenesis using the reference cell lines S. typhimurium TA 100, TA 98, TA 1537 by the Ames method showed no mutagenic activity of the preparation.

The immunotropic properties of the proposed pharmaceutical formulation were studied clinically. The study was conducted in volunteers (78 patients) including 56 subjects with various tumor diseases; 22 subjects with rheumatoid arthritis ( stages of II–III according to X-ray examination and stages II–III by their activity).

The following performances were under study: the total lymphocyte number, the number of B and T lymphocytes, the helper suppressor cell ratio; the levels of immunoglobulins C, M, A and E and circulating immune complexes; the functional activities of T and B lymphocytes (T helpers and T suppressors) in the blast-transformation reactions with a variety of mitogens, the phagocytic index and cytochemical performance of the enzymaticn activity of immunocompetent cells.

The treatment with using a pharmaceutical formulation of the invention was conducted according to the specified administration regimen. The immunologic examinations were conducted before and during the treatment (the 2 first weeks after the administration of the preparation and after one course of treatment (four weeks from the start of treatment) as well as the 2–3 months after ceasing the administration. In several cases, the immunologic performances were determined during the repeated courses of the administration of the preparation and 6 months after the start of the treatment with the proposed pharmaceutical formulation.

The improvement of the basic disease was observable in the patients upon the administration of the proposed pharmaceutical formulation for more than 2 weeks.

Subjectively, the oncologic patients reported a considerable improvement of their general conditions after conducting the course of treatment with the proposed pharmaceutical formulation. Objectively, the decrease in the tumor sizes and lymph nodes and the regeneration of intestinal evacuation was noted in several cases. After conducting the 2–3 courses of the treatment with the pharmaceutical formulation, the patients reported the improvement of their general condition and retained their labor ability; a slight weakness was associated with the necessity to keep the diet.

In most of the patients suffered from rheumatoid arthritis, the physicians reported the improvement of arthrous syndrome as the decrease in constraint after the one-course treatment using the proposed preparation. Under such conditions, the genital fibroma was disappeared in one female patient.

The examination of the patients before the treatment with a pharmaceutical formulation showed the mosaic pattern of the changes in immunologic performances in both patients with the associated diseases and patients only with the basic disease, with the values of he measured immunologic performances being within the limits of the average physiological characteristics of practically healthy humans. In most of the oncologic patients, the helper suppressor cell ratio in the subpopulations was abnormal.

The single performance changed unidirectionally in all the patients was the level of the circulating immune complexes, which was higher in both oncologic patients and subjects with rheumatoid arthritis.

After the 2-weeks administration of the proposed pharmaceutical formulation, the observation of the immunological performances showed a significant immune reaction in the patients.

In most of the patients of both groups there was observed the decrease in the total lymphocyte number, the counts of T and B lymphocytes and T helper cells, as well as the significant decrease in the number of T suppressor cells; the changes in the level of immunoglobulins of various classes were characterized by the single-sided nature in different patients, with the increase in phagocytic activity of monocytes and leukocytes revealed in the oncologic patients. The level of circulating immune complexes lowered in both oncologic patients and subjects with rheumatoid arthritis.

It should be noted that in the oncologic patients, when the helper suppressor cell ratio was abnormal, the decrease in the number of T lymphocytes and the number of their subpopulation was significantly different. This made the helper suppressor cell ratio normal even at the low functional level.

The changes of the B lymphocytes levels and, mainly the immunoglobulins of various classes were a variable character.

The studies of the proliferative lymphocytes activity in the blast-transformation reactions support the conclusion about a significant immune response upon the administration of the proposed pharmaceutical formulation, and its specific characteristics after the treatment of the patients for the first 2 week-period.

It should be pointed out that after the completion of the first course of the treatment, a significant decrease in production of the circulating antibodies was observed. With multidirectional character of changes in the other immunologic performances, it should be noted that such values are within the physiological norm.

The same picture was observable under examination of the immunologic performances in the the patients after the 2–3 month-period treatment prior to the second course of the therapy with the proposed formulation. During the repeated course, different changes in the immunologic performances in the patients were the same as those observed in the the first course of the treatment, but they had no single-sided direction in all of the patients. We tried during the study to unify patients into the groups according to the types of the changes, to link such changes to the blood groups, however, our attempts to reveal the strict regularities was unsuccessful.

The improvement of all of the studied performances in the patients was observable 6 months later after the 2–3 course treatment using the proposed pharmaceutical formulation. The comparison of the data obtained from the clinical trials concerning the immunotropic properties of the proposed pharmaceutical formulation showed a high specific character of the immune reaction in each patient. In general, the reaction undergoes the two phases. The first phase is characterized by the unidirectional changes in immunologic performances. Apparently, reconstruction of the internal regulatory mechanisms, combining immune cells into the single system, takes place under the effect of the declared agent. The second phase is associated with the normalization of the immunologic performances. Here, the general effects are as follows: decrease of the level in circulating immune complexes; the normalization of the helpers suppressor cell ratio of their subpopulation. The both phenomena are beneficial for the prognostic value, as they is indicative of returning the immunological state to norm. The decrease in the level the circulating immune complexes is observed in all of the oncologic patients and the subjects suffered from the rheumatoid arthritis. In addition, the normalization in ratios of the lymphocyte subpopulations is characteristic of the most of the patients of such groups.

The proposed pharmaceutical formulation was studied clinically in more than 250 patients. The preparation was tested in the treatment of the following diseases: malignant and innocent tumors, rheumatism, rheumatoid arthritis, bronchial asthma, neurodermitis and the like.

The main oncologic diseases were: female organs illnesses (cancer of mammary gland, carcinoma of uterine cervix and corpus, cancer of ovaries), diseases of hematopoietic system (lymphogranulomatosis, lymphoid leukosis, myelogenetic disease), diseases of the internal organs and tissues (cancer of rectum, carcinoma of the stomach,liver, cancer of the rhinopharynx, skin and the like); among the innocent tumors such as prostate adenoma, uterus fibromyoma, mammary mastopathy, cyst, rectal polyp and the like.

The patients were at the age of 20–60 year; the duration of treatment with the proposed pharmaceutical formulation was of 0.5 to 2 years and more.

A pharmaceutical formulation of the present invention was used according to the method given above: internal use—first three days 5 ml 3 times a day, then 10 ml×3 times a day for one month. Along with the administration per os, the proposed pharmaceutical formulation was applied locally depending on the pathological locus of the disease. The pharmaceutical formulation of the invention was applied locally to the pathologic locuses as lotions, tampons, syringings, enemas. The formulation was applied on the appropriate areas to be treated, including coccygeal bone, groin lymph nodes, axilla, backbone, joints, localized neoplasms, integmentary or bone-articular tissues.

The data of the treatment with using the proposed pharmaceutical formulation including including oncologic patients of stages IV, III, II (with the duration of patient's treatment varied from more than 0.5 year, more than 1 year, more than 2 years) as well the subsequent long-term supporting therapy with such formulation showed its efficiency in both untreated and prereated patients.

It was observable the complete regression of a new growth (malignant tumor), depending on the disease type, its stage and the duration of the duration of the treatments in 34,3% of patients; in 80.8% of patients with innocent tumors. In some patients stabilization of the process, decrease in tumor size were observed. An improvement of general condition was revealed in all the patients.

For a better understanding the present invention, some specific examples illustrating the preparation and clinical studies of the proposed pharmaceutical formulation are given hereinafter.

EXAMPLE 1

A pharmaceutical formulation containing the following ingredients:

| | |
|---|---|
| mercury dichloride | 0.01 g |
| white grape wine with 4% sugar content | 100 ml |

The proposed pharmaceutical formulation is prepared by the method as follows. Mercury dichloride is dissolved in dry grape wine in given amounts at conventional conditions (at room temperature) to give a clear light-yellow solution (pH=3.1). The resulting preparation is stored in dark glass bottle at the temperature not higher than 15° C. In dark place. Under storage, tartaric acid precipitate may occur, so it is necessary to agitate the solution before using.

The preparation is suited for an internal and external use.

EXAMPLE 2

A pharmaceutical formulation containing the following ingredients:

| | |
|---|---|
| mercury dichloride | 0.06 g |
| dry white grape wine with 4% sugar content | 100 ml |

A pharmaceutical formulation of the present invention is prepared similarly to the method as disclosed in Example 1. There is obtained a clear yellowish solution (pH=3.3). The preparation is suitable for internal and external use.

EXAMPLE 3

A pharmaceutical formulation containing the following ingredients:

| | |
|---|---|
| mercury dichloride | 0.1 g |
| whey with 4% sugar content | 100 ml |

A pharmaceutical formulation of the present invention is prepared similarly to the method as disclosed in Example 1. As a result, a clear light-cream solution was obtained. The preparation is suitable for internal and external use.

EXAMPLE 4

A pharmaceutical formulation containing the following ingredients:

| | |
|---|---|
| mercury dichloride | 0.3 g |
| dry white grape wine with 3% sugar content | 100 ml |

A pharmaceutical formulation of the present invention is prepared similarly to the method as disclosed in Example 1. There is obtained a clear light-yellow solution (pH=3.2). The preparation is suitable for internal and external use.

EXAMPLE 5

A pharmaceutical formulation containing the following ingredients:

| | |
|---|---|
| mercury dichloride | 1.5 g |
| whey with 3% sugar content | 100 ml |

A pharmaceutical formulation of the present invention is prepared similarly to the method as disclosed in Example 1. There is obtained a clear light-cream solution. The preparation is suitable for local application.

EXAMPLE 6

A pharmaceutical formulation containing the following ingredients:

| | |
|---|---|
| mercury dichloride | 0.25 g |
| pork fat | 230 g |
| natural honey | 240 g |
| 96° alcohol | up to 750 g |

The pharmaceutical formulation is prepared by the method as follows:

Mercury dichloride is dissolved in ethyl alcohol. Preliminary softened pork fat is mixed with natural honey in given amounts. Thereafter, the solution of mercury dichloride in ethyl alcohol is added in small portions to a mixture of pork fat with honey with rubbing carefully. The proposed pharmaceutical formulation is obtained as light-yellow cream-like product. The preparation is suitable for internal and external use.

EXAMPLE 7

The pharmaceutical formulation containing the following ingredients:

| | |
|---|---|
| potassium arsenite | 0.05 g |
| dry white grape wine with 4% sugar content | Up to 100 ml |

The pharmaceutical formulation is prepared by dissolving of potassium arsenite in dry white grape wine in given amounts. There is obtained a clear light- yellow cream solution, pH 3.2. The preparation is suitable for administration per os.

EXAMPLE 8

A pharmaceutical formulation containing the following ingredients:

| | |
|---|---|
| sodium arsenate | 0.15 |
| whey with 3% sugar content | up to 100 ml |

The pharmaceutical formulation is prepared by dissolving of sodium arsenate in whey with sugar content of 3% by weight in a given amounts. A clear solution of light-yellow colour is obtained.

The preparation is suitable for local application.

EXAMPLE 9

The pharmaceutical preparation was tested clinically in 99 oncologic patients, of them: 67 subjects have malignant tumors, 32-innocent tumors. Of the first group, 32 patients underwent a couse of pretreatment (surgical operation, multiple chemotherapy, gamma-therapy), 35—were not given the treatment earlier.

In most of the oncologic patients there was noted: IV stage of disease in 21 subjects, III stage of disease in 18; II stage was in 6 patients. In 22 patients the disease stages were not identified.

The oncologic patients were at the age of 40 to 60–39 subjects; 20 to 40–7 subjects; more than 60–14 subjects. The patients were 11 males and 56 females.

The terms of the patients treatment with the proposed pharmaceutical formulation were the following: more than 0.5 years-28 patients (41,8%), more than 1 year-3 patients (4,5%), more than 2 years-19 patients (28,3%). Long-term supporting therapy with a pharmaceutical formulation was conducted in 17 patients (25,4%). The basic diseases were the following: malignant tumors (cancer of the mammary gland, carcinoma of uterine cervix and corpus, cancer of ovaries, cancer of rectum, carcinoma of the stomach, liver, cancer of rhinopharynx, skin); diseases of the hematopoietic system (lymphogranulomatosios, lymphoid leukosis, acute lymphoblastic leukemia, myclogenetic disease); innocent tumors (prostate adenoma, uterus fibromyoma, papilloma, cyst, mastopathy of mammary glands, rectum polyps).

The following results are obtained for the oncologic patients (not treated earlier)-35 persons (100%):

complete tumor regression in 12 patients (34,3%),they became practically healthy (the diseases: cancer of the mammary gland of stages III–IV, fibrocystica mastopathia (malignant form), cancer of the uteris, cancer of ovaries, osteogenic sarcoma, melanoma, lymphoid leukosis).

the process stabilization was observed in 12 patients (34,3%). (The diseases: cancer of the mammary gland of stages III–IV, mammary adenocarcinoma, prostatic adenocarcinoma of the IV stage (metastasis in the lungs), cancer of rectum of the IV stage, cancer of rhinopharynx (metastasis in brain, vertebral column), blastoma of the esophagus lower part (malignant form, III stage).

decrease of the tumor size in 9 patients (25,8%). (The doseases: cancer of the mammary gland).

improvement of the general condition in 1 patient (2,8%).

Further progression of a disease was observable in 1 patient (2,8 %) The following results are obtained for the oncologic patients treated earlier-32 persons (100%):

complete tumor regression. Practically healthy-6 patients (18,8%). (The diseases: cancer of the mammary gland of the III–IV stages, cancer of ovaries of the IV stage, large formation of the right liver party (malignant form) basalioma of the auricle).

the process stabilization was observed in 12 patients (37,6%). (The diseases: cancer of the mammary gland, blastoma of the mammary gland, IV stage (malignant form), carcinoma cervix, cancer of the throat, III stage, cancer of the liver right part, cancer of rectum, cancer of stomatopharynx, stomach, pancreas, chronic lymphoid leukosis of the III stage, acute lymphoblasti leukosis).

decrease of the tumor size in 2 patients (6.2%). (The disease: cancer of the mammary gland).

There are no data on the relapses for 4 patients 352.5%).

improvement of the general condition in 4 patients 2.5%)

remission in 2 patients (6.2%)

satisfactory state in 1 patient (3.1%)

further progession was observable in 1 patient 3.1%).

Positive effect of the oncologic patients treatment with A pharmaceutical formulation(treated and untreated earlier) is 79%.

No effect—in one patient (2.9%).

The results of the treatment of innocent tumors (untreated earlier)-26 patients (100%):

complete tumor regression, practically healthy-21 patients (80.8%) (The diseases: fibroadenoma of the mammary gland, mastopathy, fibroma, fibromyoma of the uterine, polyp of the rectum, polyp of the uterine cervix, polycystosis, purulent tumor of ovaries, lymphoadenitis and the like.);

the process stabilization was observed in 2 patients (7.7%). (The diseases: cyst of the mammary gland, duct papilloma);

decrease of the tumor size, improvement of the general condition in 2 patients (7.6%);

satisfactory state in 1 patient (3.8%). The results of the patients (treated earlier) treatment-6 persons (100%).

practically healthy-1 person (16.7%) (The disease: mastopathy);

good condition in 3 patients (49.9%);

without relapses in 1 patient (16.7%);

remission in 1 patient (16.7%).

Positive effect of the treatment of patients with nononcologic diseases (tumors of the innocent nature) is 81%.

EXAMPLE 10

The proposed pharmaceutical formulation were studied clinically in 157 patients of which 138 (87.9%)—oncologic patients (tumors of the malignant nature); 19 (12.1%)—with tumors of the innocent nature. Of 138 oncologic patients 94 (68.1%) are after the course of preliminary treatment (operation, multiple chemotherapy, gamma-therapy), 44 patients (31.8%) without any treatment. Oncologic diseases (tumors of the malignant nature) include: I—the diseases of the female organs (cancer of the mammary gland, carcinoma of uterine cervix and corpus, cancer of ovaries)-72 patients.

II—cancer of the hematopoictic system (lymphogranulomatosis, lymphoblastic lymphoma, leukosis:chronic lymphoblasyic leukosis)-14 patients.

III—oncologic diseases of the internal organs and tissues (carcinoma of the stomach, cancer of lungs, cancer of rectum, carcinoma of the liver, cancer of the urinary bladder, cancer of the prostate and the like.)-52 patients.

The following results have been obtained in treatment patients with using a pharmaceutical formulation of the present invention. For the group of the oncologic patients (tumors of the malignant nature) of stages II, III, IV-138 persons (100%) it was determined:

complete tumor regression in 5 patients (3.6%);

decrease of the tumor size in 32 patients (23.5%);

stabilization of the malignant tumor growth in 28 patients (20.3%);

further disease progression in 12 patients (8.7%).

For the group of the patients with tumors of the innocent nature-19 persons (100%) it was determined:

regression of the tumor in 8 patients (42.1%);

stabilization of the process in 5 patients (26.2%);

decrease of the tumor size in 4 patients (21.1%);

improvement in 2 patients (10.5%).

Industrial applicability

A pharmaceutical formulation can be used in medicine for treatment of various immunodeficient conditions, all types of malignant and innocent tumors, rheumatism, rheumatoid arthritis, polyarthritis, bronchial astma; systemic lupus erythematosis, gastric ulcera, herpes, gravitational ulcera, psoriasis, intestinal infections, neurodermites and the like.

What is claimed is:

1. A pharmaceutical formulation having an immunomodulating and regenerating effect on a defective function of cell tissue division-regulating system comprising an active ingredient and a diluent, wherein said pharmaceutical formulation contains from 0.01 to 1.5 percent by weight mercury dichloride or potassium arsenite, or sodium arsenate as an active ingredient and from 98.5 to 99.99 percent by weight diluent, wherein said pharmaceutical formulation further comprises dry white grape wine with sugar content of 3–4% by weight or whey with sugar content of 3–4% by weight as said diluent.

2. A pharmaceutical formulation having an immunomodulating and regenerating effect on a defective function of cell tissue division-regulating system comprising an active ingredient and a diluent, wherein said pharmaceutical formulation contains from 0.01 to 1.5 percent by weight mercury dichloride or potassium arsenite, or sodium arsenate as an active ingredient and from 98.5 to 99.99 percent by weight diluent, wherein said pharmaceutical formulation comprises the following ingredients, % by weight:

| | |
|---|---|
| mercury dichloride | 0.01%–0.1% and 99.9 to 99.99% of dry white grape wine with sugar content of 3–4% by weight or 99.9 to 99.99% whey sugar content of 3–4% by weight. |

3. A pharmaceutical formulation having an immunomodulating and regenerating effect on a defective function of cell tissue division-regulating system comprising an active ingredient and a diluent, wherein said pharmaceutical formulation contains from 0.01 to 1.5 percent by weight mercury dichloride or potassium arsenite, or sodium arsenate as an active ingredient and from 98.5 to 99.99 percent by weight diluent, wherein said pharmaceutical formulation contains a mixture of pork fat, natural honey and ethyl alcohol as diluent at the following mixture ratio, % by weight:

| | |
|---|---|
| mercury dichloride | 0.03–0.13%, |
| pork fat | 30.7–37.3%, |
| natural honey | 30.7–37.3%, |
| ethyl alcohol | q.s. |

4. A pharmaceutical formulation having an immunomodulating and regenerating effect on a defective function of cell tissue division-regulating system comprising an active ingredient and a diluent, wherein said pharmaceutical formulation contains from 0.01 to 1.5 percent by weight mercury dichloride or potassium arsenite, or sodium arsenate as an active ingredient and from 98.5 to 99.99 percent by weight diluent, wherein said pharmaceutical formulation comprises the following ingredients, % by weight:

sodium arsenate or potassium arsenite 0.05–0.15% and 99.85 to 99.95% of dry white grape wine with sugar content of 3–4% by weight or 99.85 to 99.95% whey with sugar content of 3–4% by weight.

5. A pharmaceutical formulation having an immunomodulating and regenerating effect on a defective function of cell tissue division-regulating system comprising an active ingredient and a diluent, wherein said pharmaceutical formulation contains from 0.01 to 1.5 percent by weight mercury dichloride or potassium arsenite, or sodium arsenate as an active ingredient and from 98.5 to 99.99 percent by weight diluent, wherein said pharmaceutical formulation comprises the following ingredients, % by weight:

| | |
|---|---|
| mercury dichloride | 0.3–1.5%, |
| a 3–4% sugar-content dry white grape wine, or | |
| a 3–4% sugar-content whey to the 100% balance. | | a 3–4% sugar-content dry white grape wine, or a 3–4% sugar-content whey to the 100% balance.

* * * * *